(12) United States Patent
You et al.

(10) Patent No.: US 12,140,547 B2
(45) Date of Patent: Nov. 12, 2024

(54) DIGITAL SURFACE-ENHANCED RAMAN SPECTROSCOPY SENSING PLATFORM

(71) Applicants: KOREA RESEARCH INSTITUTE OF STANDARDS AND SCIENCE, Daejeon (KR); VIRGINIA TECH INTELLECTUAL PROPERTIES, INC., Blacksburg, VA (US)

(72) Inventors: Eun-Ah You, Daejeon (KR); Zhou Wei, Blacksburg, VA (US); Wonil Nam, Busan (KR); Wansun Kim, Namyangju-si (KR)

(73) Assignees: KOREA RESEARCH INSTITUTE OF STANDARDS AND SCIENCE, Daejeon (KR); VIRGINIA TECH INTELLECTUAL PROPERTIES, INC., Blacksburg, VA (US)

(*) Notice: Subject to any disclaimer, the term of this patent is extended or adjusted under 35 U.S.C. 154(b) by 0 days.

(21) Appl. No.: 17/587,541

(22) Filed: Jan. 28, 2022

(65) Prior Publication Data

US 2023/0168201 A1   Jun. 1, 2023

(30) Foreign Application Priority Data

Nov. 29, 2021   (KR) .................. 10-2021-0167646

(51) Int. Cl.
*G01N 21/65* (2006.01)
*B82Y 35/00* (2011.01)
(Continued)

(52) U.S. Cl.
CPC ....... *G01N 21/658* (2013.01); *G01N 33/6896* (2013.01); *B82Y 35/00* (2013.01); *B82Y 40/00* (2013.01); *G01N 2021/656* (2013.01)

(58) Field of Classification Search
None
See application file for complete search history.

(56) References Cited

U.S. PATENT DOCUMENTS 7,271,896 B2 *  9/2007  Chan ................ G01N 21/65
                                                    436/164
8,821,978 B2 *  9/2014  Cheng .............. B81C 1/00031
                                                    430/323
(Continued)

FOREIGN PATENT DOCUMENTS

KR         101272316 B1 *  6/2013
KR         20130003843 U   6/2013
(Continued)

OTHER PUBLICATIONS

Zhang, K., et al. "Quantitative SERS detection of dopamine in cerebrospinal fluid by dual-recognition-induced hot spot generation." ACS applied materials & interfaces 10.18 (2018): 15388-15394 (Year: 2018).*

(Continued)

*Primary Examiner* — Tarifur R Chowdhury
*Assistant Examiner* — Roberto Fabian, Jr.
(74) *Attorney, Agent, or Firm* — Hauptman Ham, LLP (57) ABSTRACT

The present disclosure relates to a surface-enhanced Raman spectroscopy complex probe capable of effectively detecting a catecholamine compound even at extremely low concentrations. The complex probe includes a nanolaminate including a nanogap and metal nanoparticles. In this case, the nanolaminate and the metal nanoparticles are modified to a compound that may be bound to each functional group included in catecholamine, and thus, catecholamine included in an analyte is doubly recognized by the complex probe. In addition, since a hotspot emitting a strong SERS signal is formed by a nanogap included in a nanolaminate, (Continued)

it is possible to effectively detect a catecholamine compound even at extremely low concentrations.

10 Claims, 13 Drawing Sheets

(51) Int. Cl.
    *B82Y 40/00*     (2011.01)
    *G01N 33/68*     (2006.01)

(56) References Cited

U.S. PATENT DOCUMENTS

| | | |
|---|---|---|
| 9,052,598 B2 * | 6/2015 | Wu .................. G03F 7/2037 |
| 2003/0138375 A1 * | 7/2003 | Leyland-Jones ... A61K 49/0004 |
| | | 435/7.1 |
| 2014/0011691 A1 * | 1/2014 | Sierks ................ C07K 16/005 |
| | | 506/18 |

FOREIGN PATENT DOCUMENTS

| | | |
|---|---|---|
| KR | 20170129633 A | 11/2017 |
| KR | 20180052101 A | 5/2018 |
| KR | 20210028988 A | 3/2021 |

OTHER PUBLICATIONS

Tahir, M. A., et al. "Surface-enhanced Raman spectroscopy for bioanalysis and diagnosis." Nanoscale 13.27 (2021): 11593-11634 (Year: 2021).*

Song, J. et al. "Scalable high-performance nanolaminated SERS substrates based on multistack vertically oriented plasmonic nanogaps." Advanced Materials Technologies 4.5 (2019): 1800689 (Year: 2019).*

Zhang et al., "Quantitative SERS Detection of Dopamine in Cerebrospinal Fluid by Dual-Recognition Induced Hot Spot Generation," ACS Applied Materials & Interfaces, 8 pages.

Tahir et al., "Surface-enhanced Raman spectroscopy for bioanalysis and diagnosis," Royal Society of Chemistry, Nanoscale, 2021, 13, 11593-11634 pages.

Korean Office Action issued in corresponding Korean Patent Application No. 10-2021-0167646 on Aug. 10, 2022, pp. 1-8.

Korean Notice of Allowance issued in corresponding Korean Patent Application No. 10-2021-0167646 on Nov. 23, 2022, pp. 1-7.

[Supportive materials for Exception to Loss of Novelty] Wonil Nam et al., "A digital SERS sensing platform using 3D nanolaminate plasmonic crystals coupled with Au nanoparticles for accurate quantitative detection of dopamine", The Royal Society of Chemistry, Sep. 7, 2021, 10 pages.

[Supportive materials for Exception to Loss of Novelty] Eun-Ah You et al., "Accurately measure dopamine concentration with digital signal technique", Korea Research Institute of Standards and Science, Nov. 17, 2021, 7 pages. Machine translated English Abstract.

Shilpi Verma et al., "ZnO-rGO nanocomposite based bioelectrode for sensitive and ultrafast detection of dopamine in human serum", Biosensors and Bioelectronics, Jun. 5, 2020, 8 pages, cited in the Specification.

* cited by examiner

DIGITAL SURFACE-ENHANCED RAMAN SPECTROSCOPY SENSING PLATFORM

CROSS-REFERENCE TO RELATED APPLICATIONS

This application claims priority under 35 U.S.C. § 119 to Korean Patent Application No. 10-2021-0167646, filed on Nov. 29, 2021, in the Korean Intellectual Property Office, the disclosure of which is incorporated herein by reference in its entirety.

TECHNICAL FIELD

The following disclosure relates to a surface-enhanced Raman spectroscopy complex probe including a nanolaminate and metal nanoparticles, and a method of detecting catecholamine using the same.

BACKGROUND

Dopamine (DA) is one of the most important neurotransmitters, playing critical roles in various physiological and brain activities. For example, the DA has been used as a crucial biomarker in medical diagnostics because abnormal DA levels have been observed in patients suffering from diverse neurological disorders such as Parkinson's disease, schizophrenia, attention deficit hyperactivity disorder, Huntington's disease, and epilepsy. In addition to its neural communication role, the DA is also involved in immuno-regulation, modulating the metabolism and the immune system. Therefore, the need for a technology to quantitatively detect such DA is increasing.

Although various conventional DA detection methods have been developed, including electrochemistry, chromatography, chemiluminescence, fluorescence, surface plasmon resonance, and plasmonic colorimetry, the majority of DA sensing platforms can only reliably measure DA down to the nanomolar range, which is not sufficient for the diagnosis of neurological disorders requiring a sensitivity down to tens of picomolar range.

Recently, several sensors have demonstrated improved sensitivity down to 1 pM. Of these, electrochemical sensors are one (S. Verma et al., Biosens. Bioeletron., 2020, 167, 112347) of the most well-established techniques due to their high sensitivity and rapid detection. However, this approach suffers from low selectivity because of the presence of electroactive interferents in extracellular fluids (for example, ascorbic acid and uric acid) which are oxidized by a very similar potential to that for DA.

Surface-enhanced Raman spectroscopy (SERS) has emerged as a promising biochemical detection technique, providing molecular fingerprint information with a rapid, non-destructive, and ultrasensitive detection capability down to the single-molecule level. The SERS is a technique of exploiting the surface plasmon enhancement of both the excitation and inelastic Raman scattering processes of molecules at plasmonic hotspots, dramatically amplifying intrinsically weak Raman scattering signals.

Although various conventional label-free SERS platforms have been used to detect DA in extracellular physiological fluids, the label-free SERS approach still faces significant challenges in diagnostic applications due to its lack of specificity and low sensitivity. For mitigating these issues, sample pre-treatment and chemical functionalization have been used to selectively extract DA from extracellular physiological fluids. The method has somewhat improved the above issues, but still remains at the nanomolar level in detecting the DA because DA molecules have a weak Raman scattering cross-section.

SUMMARY

An exemplary embodiment is directed to providing a surface-enhanced Raman complex probe as a surface-enhanced Raman double recognition platform capable of effectively detecting a catecholamine compound even at extremely low concentrations.

Another exemplary embodiment is directed to providing a composition for biosensing or bioimaging capable of effectively detecting a catecholamine compound.

Still another exemplary embodiment is directed to providing a method of detecting catecholamine using a surface-enhanced Raman complex probe.

Still yet another exemplary embodiment is directed to providing a method of providing information necessary for a disease of a neurological disease using a surface-enhanced Raman complex probe.

To achieve the object,?

In some implementation, a surface-enhanced Raman spectroscopy complex probe for detecting catecholamine includes: a nanolaminate including a nanogap, a surface of the nanolaminate being modified with a compound that binds to a first functional group of the catecholamine; and a metal nanoparticle whose surface is modified with a compound that binds to a second functional group of the catecholamine.

In some implementation, there is provided a composition for biosensing or bioimaging including the surface-enhanced Raman spectroscopy complex probe.

In some implementation, there is provided a method of detecting catecholamine included in an analyte, using a surface-enhanced Raman spectroscopy complex probe.

In some implementation there is provided a method of providing information necessary for a diagnosis of neurological diseases using a surface-enhanced Raman spectroscopy complex probe.

DETAILED DESCRIPTION OF EMBODIMENTS

Hereinafter, the present invention will be described below.

Meanwhile, exemplary embodiments in the present disclosure may be modified in several other forms, and the scope of the present disclosure is not limited to exemplary embodiments to be described below. Rather, these exemplary embodiments are provided so that this disclosure will be thorough and complete, and will fully convey the concept of the invention to those skilled in the art. Furthermore, throughout the present specification, unless explicitly described to the contrary, "including" any components will be understood to imply the inclusion of other elements rather than the exclusion of any other elements.

An exemplary embodiment of the present disclosure provides a surface-enhanced Raman spectroscopy complex probe, including: a nanolaminate including a nanogap, a surface of the nanolaminate being modified with a compound that binds to a first functional group of catecholamine; and a metal nanoparticle whose surface is modified with a compound that binds to a second functional group of the catecholamine.

In an exemplary embodiment, the first functional group and the second functional group may be each selected from an amine group and a diol group, which are two functional groups commonly included in catecholamine-based compounds. That is, when any one of the amine group and the diol group is selected as the first functional group, the second functional group may be the other functional group not selected from the first functional group.

In an exemplary embodiment, the compound capable of binding to the amine group of the catecholamine may be a compound including a leaving group capable of being separated by binding to the amine group of catecholamine. For example, an example of the compound may include 3,3'-dithiodipropionic acid di(N-hydroxysuccinimide ester) (DSP), but when the compound is a compound to which the amine group binds, the compound is not particularly limited as long as it can bind to the catecholamine in an exemplary embodiment of the present disclosure. In an exemplary embodiment, the compound capable of binding to the diol group of catecholamine is not particularly limited as long as it is a compound capable of binding to the diol group of the catecholamine. An example of the compound may be a compound including a $B(OH)_2$ group such as 3-mercaptophenylboronic acid (3-MPBA).

When the compound capable of binding to the amine group and/or the compound capable of binding to the diol group may effectively bind to a nanolaminate and/or metal nanoparticles when having —S— binding.

In an exemplary embodiment, the nanolaminate may include a plasmonic metal layer and an etching layer. In this case, the plasmonic metal layer and the etching layer may be alternately stacked with each other. In an exemplary embodiment, the nanogap may be formed between the plasmonic metal layer and the etching layer, and specifically, the nanogap may be formed in the space between the plasmonic metal layer and the etching layer formed by etching the etching layer using a buffered oxide etchant (BOE) solution.

The etching layer is not necessarily limited as long as it is a layer etched through an etching process such as etching or lithography, and may be, for example, an oxide film or a nitride film, or $SiO_2$, SiN, or $Si_3N_4$. Alternatively, for example, the etching layer may use a layer commonly used as a dielectric layer or an insulating layer.

In an exemplary embodiment, the plasmonic metal layer and the etching layer may be vertically stacked. The plasmonic metal layer may be stacked to a thickness of, for example, 10 nm to 50 nm, 20 nm to 40 nm, or 25 nm to 35 nm, but is not limited thereto. The etching layer may be stacked to a thickness of, for example, 5 nm to 30 nm, 10 nm to 25 nm, or 10 nm to 20 nm, but is not limited thereto. The thicknesses of the plasmonic metal layer and the etching layer are not necessarily the same in each stacked layer, but may have independent thicknesses.

In an exemplary embodiment, the nanogap may have a width of 0.1 nm to 100 nm. Alternatively, for example, the nanogap may have a thickness of 0.1 nm to 80 nm, 0.1 nm to 60 nm, 0.1 nm to 40 nm, 0.1 nm to 20 nm, 1 nm to 20 nm, or 5 nm to 15 nm, but is not limited thereto. In this case, the width of the nanogap may be determined in consideration of a diameter of a suitable metal nanoparticle to form an additional hotspot by binding the metal nanoparticles to the nanogap hotspot.

In an exemplary embodiment, the metal nanoparticles may be, for example, nanoparticles of plasmonic metal, and specifically, may be gold (Au), silver (Ag), copper (Cu), aluminum (Al), platinum (Pt), or palladium (Pd).

In an exemplary embodiment, an average diameter of the metal nanoparticles may be 1 nm to 100 nm, or, for example, 1 nm to 80 nm, 1 nm to 60 nm, 1 nm to 40 nm, 1 nm to 20 nm, or 5 nm or 20 nm. The average diameter of the metal nanoparticles may be appropriately determined in consideration of biocompatibility.

In an exemplary embodiment, the catecholamine may be doubly recognized by binding to both the first functional group and the second functional group included in the complex probe, and thus, may be more effectively detected. More specifically, the catecholamine may be doubly recognized by binding, for example, the modified compound and the diol group of the catecholamine to the metal nanoparticles, and the modified compound and the amine group of the catecholamine to the nanolaminate, and a very strong SERS signal may be generated by forming a reinforced hotspot in the nanogap included in the nanolaminate, so it is possible to quantitatively detect even catecholamine having an extremely low concentration of a pico level by the complex probe.

In an exemplary embodiment, when the catecholamine is a catecholamine-based compound having a diol group and an amine group, the catecholamine can be detected by the complex probe according to an exemplary embodiment of the present disclosure, and therefore, it is not necessarily limited to a specific catecholamine-based compound. Specific examples of catecholamine compounds detectable by the complex probe according to an exemplary embodiment include dopamine, polydopamine, alpha-methyldopamine, norepinephrine, epinephrine, methyldopa, droxidopa, or 5-hydroxydopamine, and even a combination of these can be detected.

Figure 12:
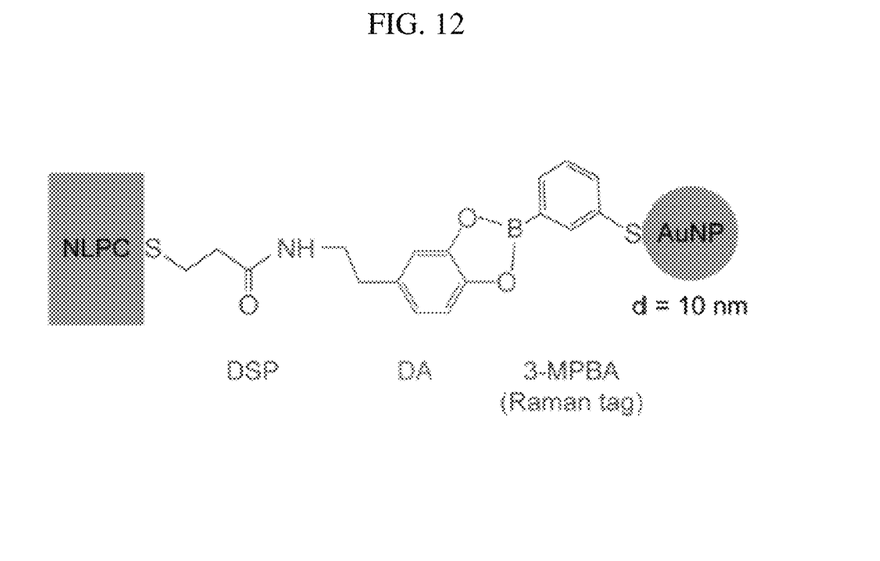
FIG. 12 is a diagram illustrating a binding relationship of DSP-NLPC, DA, and 3-MPBA-AuNP.

In an exemplary embodiment, a binding relationship of the dopamine molecules, and a substrate including a nanolaminate modified with DSP capable of binding to an amine group which is included in a dopamine molecule as an example of the catecholamine and metal nanoparticles modified with 3-MPBA capable of binding to the diol group is illustrated as an example in FIG. 12.

Figure 13:
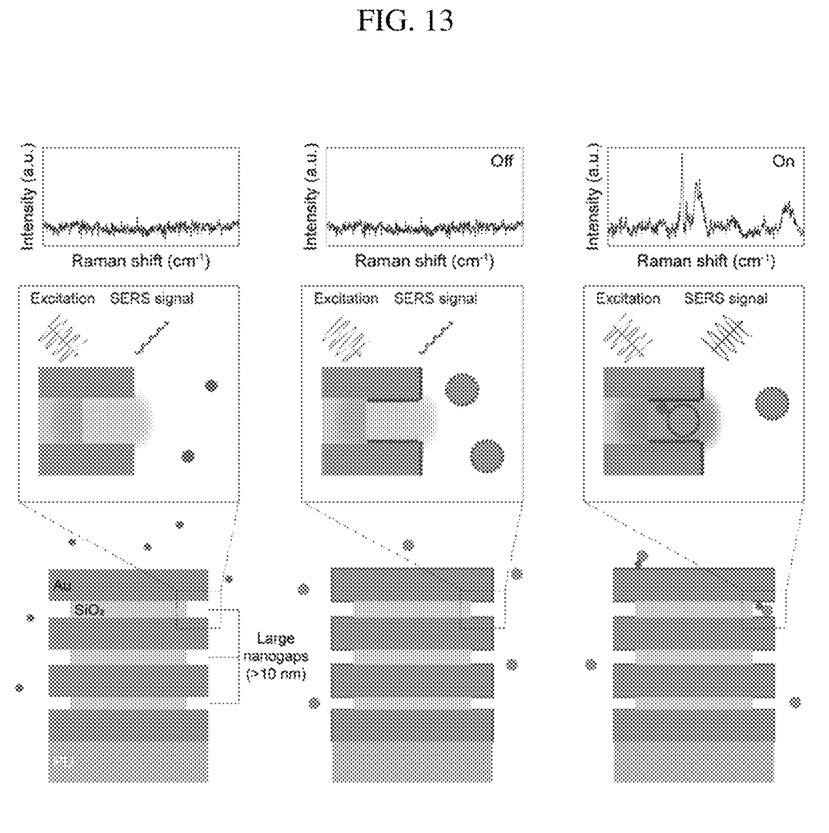
FIG. 13 is a diagram illustrating DSP-NLPC+3-MPBA-AuNP in the absence of dopamine when the surface is not modified with Raman-tag (left), that is, an "OFF" state (middle), and DSP-NLPC+3-MPBA-AuNP in the presence of dopamine, that is, an "ON" state (right).

FIG. 13 is a diagram illustrating DSP-NLPC+3-MPBA-AuNP in the absence of dopamine when the surface is not modified to Raman-tag (left), that is, an "OFF" state (middle), and DSP-NLPC+3-MPBA-AuNP in the presence of dopamine, that is, an "ON" state (right). It can be seen that, when the dopamine is present, a stronger signal is generated by adding the hotspot by the metal nanoparticles to the hotspot of the metal plasmon layer formed in the nanogap.

An exemplary embodiment of the present disclosure provides a composition for biosensing or a composition for bioimaging including the surface-enhanced Raman complex probe.

In an exemplary embodiment, the composition for biosensing may be a composition for sensing catecholamine from an analyte, and the composition for bioimaging may be a composition for imaging catecholamine included in the analyte.

Another exemplary embodiment of the present disclosure provides a method of detecting catecholamine included an analyte using a surface-enhanced Raman spectroscopy complex probe, including: a nanolaminate including a nanogap, the surface of the nanolaminate being modified with a compound binding to an amine group; and metal nanoparticles whose surface is modified with a compound binding to a diol group.

In an exemplary embodiment, the catecholamine can be quantitatively detected even at an extremely low concentration of pico level, and for example, 0.1 pM or more, 0.5 pM or more, 1 pM or more, 10 pM or more of catecholamine can also be detected.

In an exemplary embodiment, the detection method may include incubating the laminate and the metal nanoparticles together with the analyte. Alternatively, the detection method may include incubating the laminate or the substrate including the laminate together with the analyte to bind the substrate to the catecholamine included in the analyte; removing unbound catecholamine through a washing process; incubating with the metal nanoparticles to bind the catecholamine binding to the substrate and the metal nanoparticles; and removing the unbound catecholamine through the washing process.

In an exemplary embodiment, the excitation light (irradiated light) used for detection of the catecholamine may have a wavelength of 500 nm to 1500 nm, or, for example, 600 nm to 1300 nm, 600 nm to 1000 nm, or 600 nm to 900 nm.

Another exemplary embodiment of the present disclosure provides a method of providing information necessary for a diagnosis of neurological diseases using a surface-enhanced Raman spectroscopy complex probe, including: a nanolaminate including a nanogap, the surface of the nanolaminate being modified with a compound binding to an amine group; and metal nanoparticles whose surface is modified with a compound binding to a diol group.

In this case, the neurological disease may be Parkinson's disease, schizophrenia, attention deficit hyperactivity disorder, Huntington's disease, Lou Gehrig's disease, stroke, dementia, or epilepsy, and the neurological disease is not limited thereto as long as it is a neurological disease characterized in that catecholamine is secreted.

In an exemplary embodiment, the complex probe quantitatively detects the catecholamine included in the analyte, thereby providing information necessary for diagnosis of a neurological disease.

In this case, the analyte may be extracted from an individual with suspected neurological disease.

Hereinafter, Examples and Experimental Examples of the present invention will be specifically illustrated and described below. However, the Examples and Experimental Examples to be described below are merely illustrative of a part of the present invention, and the present invention is not limited thereto.

<Example 1> Manufacturing of Substrate Including Nanolaminate

A substrate including nanolaminate, which is included in the surface-enhanced Raman spectroscopy complex probe, was manufactured by the following method.

1-1. Preparation of 3D Nanolaminate Plasmonic Crystal (NLPC)

Figure 1:
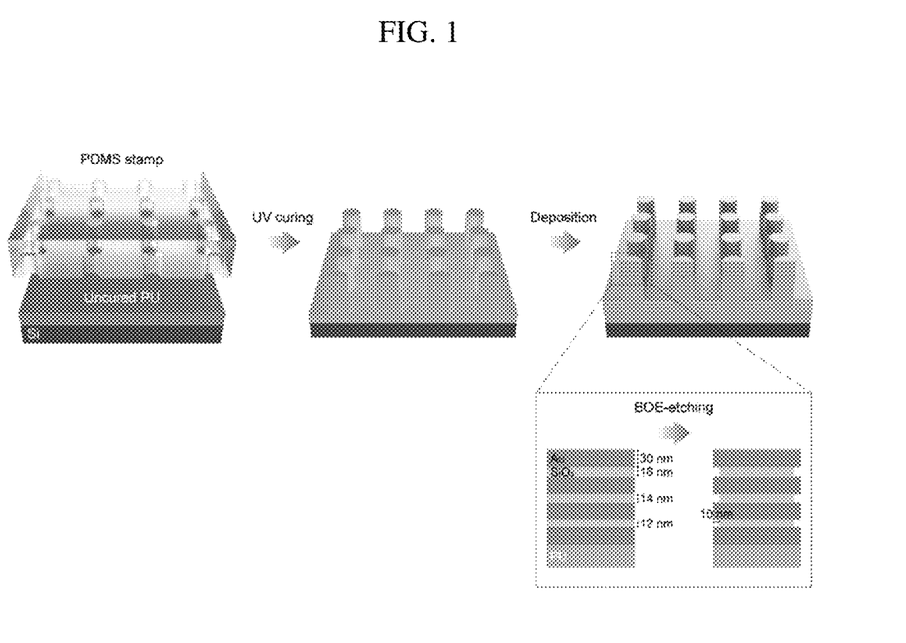
FIG. 1 is a diagram illustrating a process for manufacturing a substrate including a nanolaminate.
Figure 2:
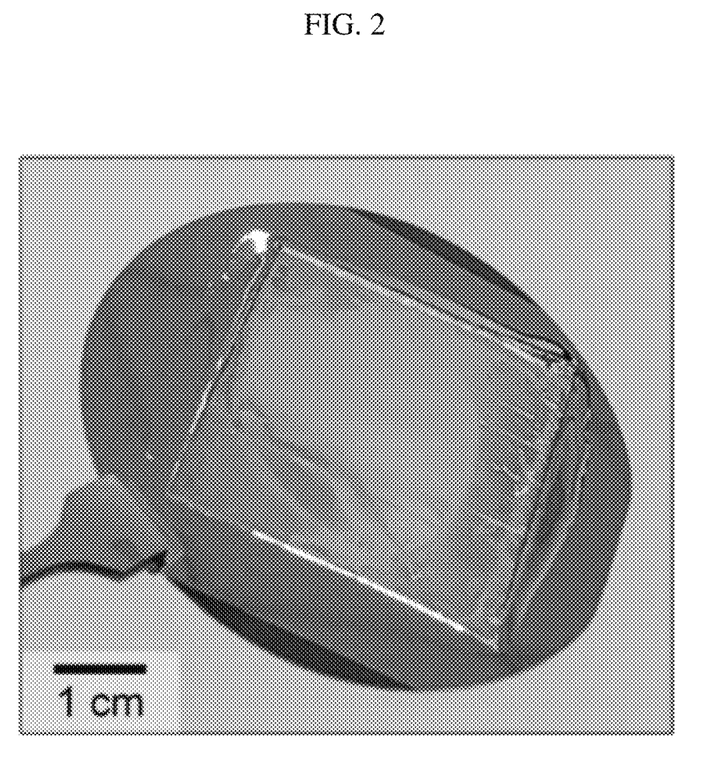
FIG. 2 is a photograph of the substrate including the nanolaminate manufactured in 1-1. of Example 1, in which a clear light diffraction pattern may be confirmed due to a uniform distribution of a nanopillar array at regular intervals.
Figure 3:
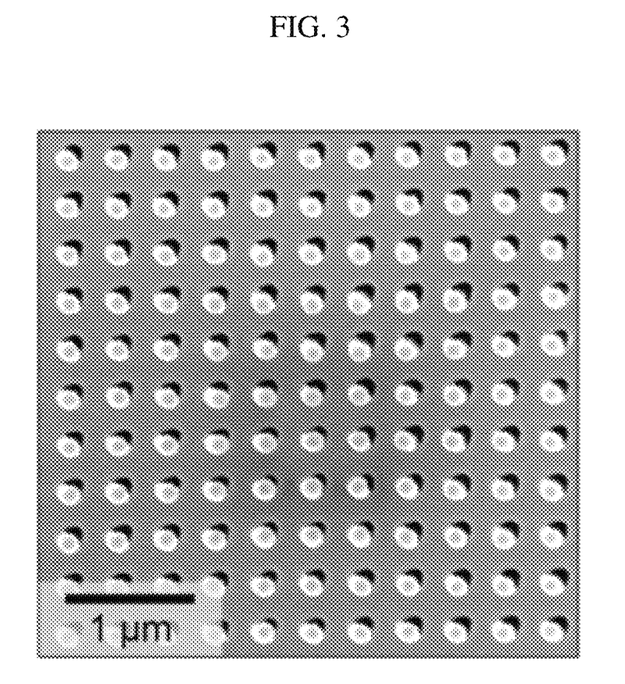
FIG. 3 is an image of a plane of the substrate including the nanolaminate manufactured in 1-1. of Example 1 with a scanning microscope (SEM).

First, in order to generate a nanopillar array at regular intervals, a complex polydimethylsiloxane (PDMS) stamp patterned with a nanohole array (diameter=150 nm, spacing=400 nm, height=400 nm) using soft lithography was prepared. The PDMS has two layers, and a lower layer is a harder layer called hard-PDMS, and was prepared by spin-coating hard-PDMS on a silane-coated silicon master and then curing the hard-PDMS at 60° C. for 10 minutes. Next, after liquid PDMS was poured on the hard-PDMS and cured for 4 hours, UV-curable polyurethane (NOA61, Norland Product Inc., USA) on a 3-inch silicon wafer was UV-cured for 10 minutes to solidify with the PDMS stamp, and then heat-cured overnight in a convection oven at 80° C. (FIG. 1).

Next, a 1 nm-thick Cr layer was deposited as an adhesive layer on the nanopillar array, and a 1 nm-thick Ti layer was deposited on all metal-dielectric interfaces. Then, to generate the nanolaminate on the nanopillar array, four gold (Au) nanoparticles layers with a thickness of 30 nm and three $SiO_2$ layers having a thickness 12, 14, and 16 nm were alternately deposited using an electron beam evaporator (PVD250, Kurt J. Lesker Company, USA). To form the nanogap in the nanolaminate, 10:1 BOE (Transene Inc., USA) was treated for 10 seconds to partially etch the $SiO_2$ layer so that molecules and gold nanoparticles could access the nanogap hotspot region (FIG. 1).

1-2. Surface Modification

In order to modify the surface of the nanolaminate prepared in 1-1. with a compound binding to catecholamine, 3,3'-dithiodipropionic acid di(N-hydroxysuccinimide ester) (DSP) was used as an example of a compound binding to an amine group among functional groups included in the catecholamine.

Specifically, the substrate manufactured in 1-1. above was functionalized with 1 mL of 5 mM DSP in DMSO for 100 minutes, and then washed with DMSO and deionized water, respectively, for 5 min to remove residual DSP, so the substrate including the nanolaminate whose surface is modified with the DSP was manufactured.

<Example 2> Preparation of Natal Nanoparticles

In order to modify the surface of metal nanoparticles with a compound binding to catecholamine, 3-mercaptophenylboronic acid (3-MPBA) was used as an example of a compound binding to a diol group among functional groups included in the catecholamine.

Specifically, 30 μL of 1 mM 3-MPBA (in 0.2 M NaOH) was added to 1 mL of 10 nm AuNPs (diameter: 10 nm) and reacted at room temperature for 1 hour. Then, to remove unbound 3-MPBA, 3-MPBA-modified AuNPs (3-MPBA-AuNPs) were collected by centrifugation at 15,000 rpm for 10 minutes, and then 3-MPBA-AuNPs were resuspended in deionized water and rinsed three times, so metal nanoparticles whose surface is modified with 3-MPBA were prepared.

<Experimental Example 1> Performance Evaluation of Complex Probe

Hereinafter, in order to prepare the complex probe used in the experiment, dopamine (DA) was used as an example as a catecholamine compound. And the substrate (DSP-NLPC) whose surface is modified with the DSP manufactured in Example 1 was incubated with various concentrations of dopamine in artificial CSF (aCSF) of pH 7.4 (1 mL) at room temperature for 1 hour, washed in deionized water for 5 minutes to remove unbound dopamine molecules, incubated the dopamine-binding DSP-NLPC substrate with 200 μL of 3-MPBA-AuNP for 1 hour, and then washed with deionized water for 5 minutes to remove unbound 3-MPBA-AuNP, and was used.

1-1. SERB Intensity Evaluation

Figure 4:
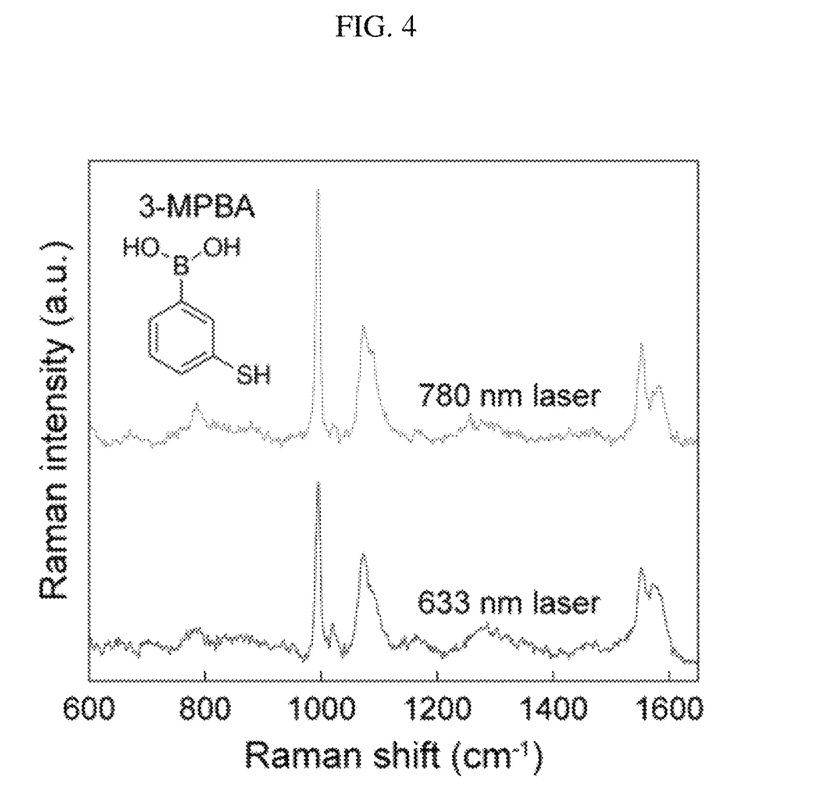
FIG. 4 is a diagram illustrating Raman spectra of 3-MPBA-NLPC at 780 nm and 633 nm wavelengths.

As a result of measuring the 3-MPBA molecule on the substrate using two excitation wavelengths of 633 nm and 780 nm, the SERS intensity of 3-MPBA at 994 cm$^{-1}$ was relatively higher for excitation of 780 nm than excitation of 633 nm (FIG. 4).

1-2. FDTD Analysis

Figure 5:
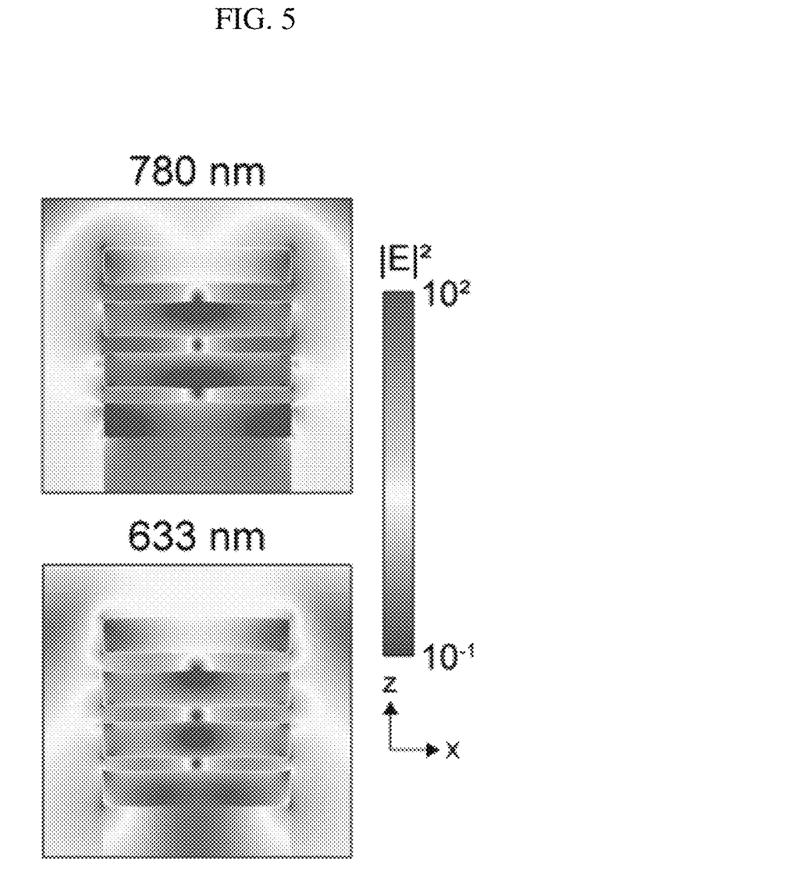
FIG. 5 is a diagram illustrating finite-difference time-domain simulation (FDTD) analysis results of 3-MPBA-NLPC at a wavelength of 780 nm and a wavelength of 633 nm.

As a result of investigating near-field optical properties of NLPC using FDTD (Lumerical Inc) simulation, it was found that a stronger local electric field was concentrated in a nanogap and a sidewall of a metal nanodisk at the excitation wavelength of 780 nm compared to 633 nm (FIG. 5). Since it is shown that SERS intensity is higher at 780 nm, an excitation wavelength of 780 nm was used for further investigation of the NLPC-based SERS activity below.

1-3. Raman Spectrum Analysis

Figure 6:
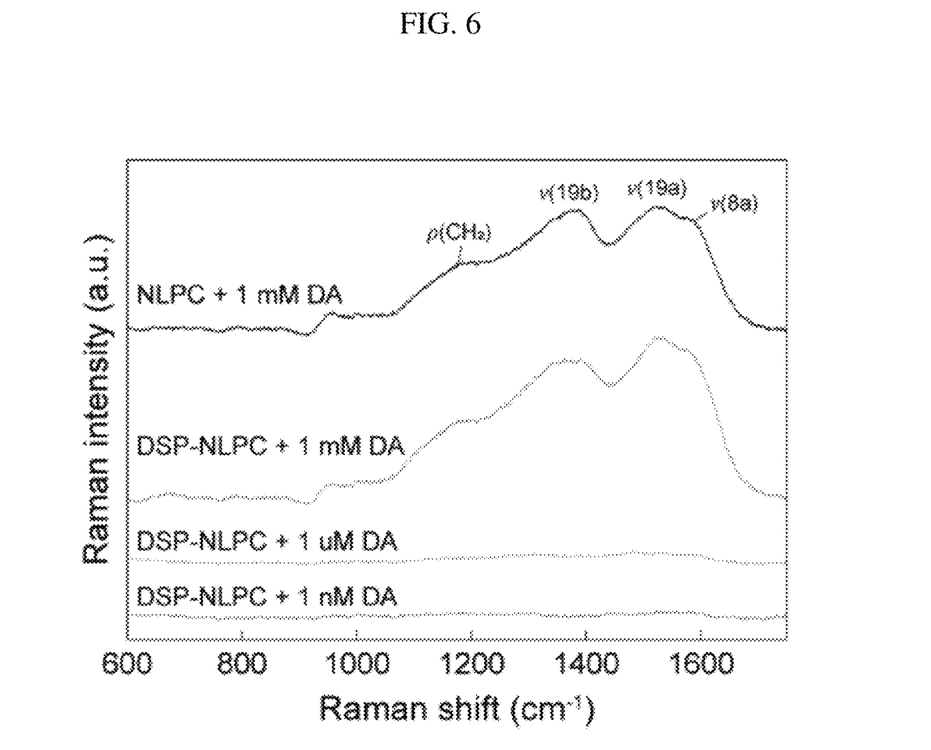
FIG. 6 is a diagram illustrating results of Raman spectrum analysis of NLPC and DSP-NLPC at various dopamine concentrations.

The results of evaluating the SERS activity of the substrate were shown in FIG. 6. As a result of measuring SERS after incubating a substrate (NLPC) including nanolaminate whose surface is not modified and a substrate (DSP-NLPC) including nanolaminate whose surface is modified, respectively, with dopamine (DA) which is a catecholamine compound, the NLPC showed several broad and overlapping Raman peaks, whereas the DSP-NLPC showed about 1.3 times higher peak intensity than label-free SERS (NLPC) detection at 1525 cm$^{-1}$ at the same concentration (1 mM). It can be seen that DSP-mediated dopamine may bind to the NLPC substrate more effectively. In addition, a change showed in a ratio of two characteristic peaks of dopamine at 1380 cm$^{-1}$ and 1525 cm$^{-1}$ because an orientation of dopamine with respect to a local field of the hotspot was modulated by the dopamine binding to the DSP-NLPC substrate.

Figure 7:
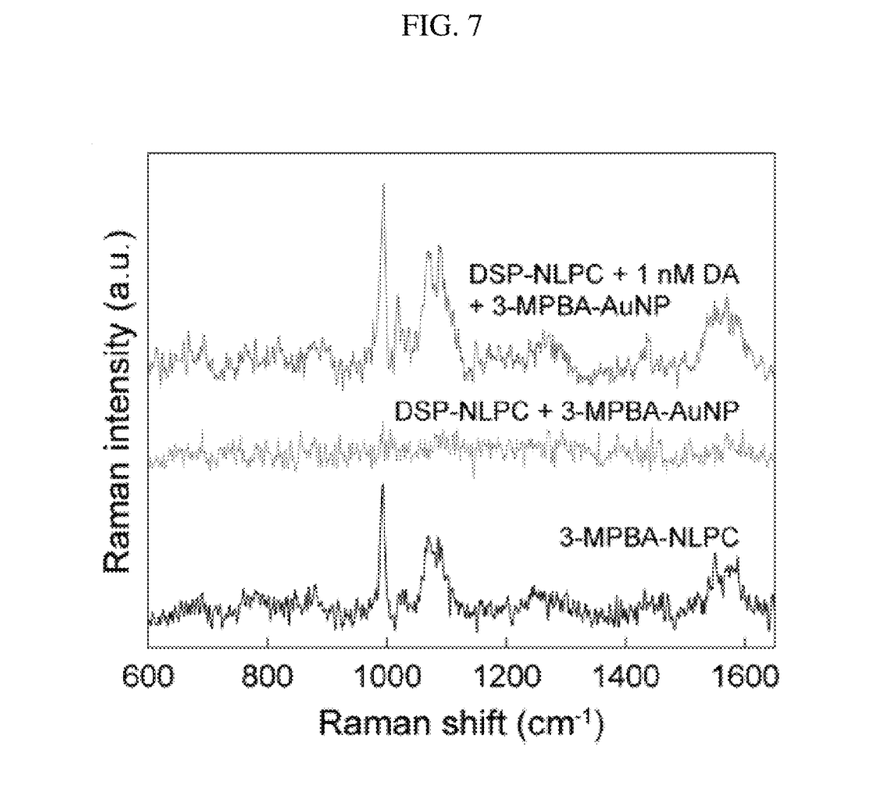
FIG. 7 is a diagram illustrating the results of analyzing Raman spectra of DSP-NLPC+DA+3-MPBA-AuNP, DSP-NLPC+3-MPBA-AuNP, and 3-MPBA-NLPC.

The result of analyzing the Raman spectrum of the complex probe was illustrated in FIG. 7. As a result of measuring the Raman spectra of 3-MPBA-NLPC, DS-NLPC+3-MPBA-AuNP, DSP-NLPC+1 nM DA+3-MPBA-AuNP, the Raman spectra of DSP-NLPC+1 nM DA+3-MPBA-AuNP clearly showed the main characteristic peaks of 3-MPBA at 994 cm$^{-1}$ and 1071 cm$^{-1}$, and it was confirmed that the intensity was increased by the hotspot induced by AuNP. Meanwhile, in the case of the DS-NLPC+3-MPBA-AuNP, the peaks related to the DSP or 3-MPBA did not appear because the 3-MPBA-AuNP may not bind to the substrate without dopamine molecules.

<Experimental Example 2> Quantitative Detection Analysis of Catecholamine Compound (Digital SERB Detection)

Figure 8:
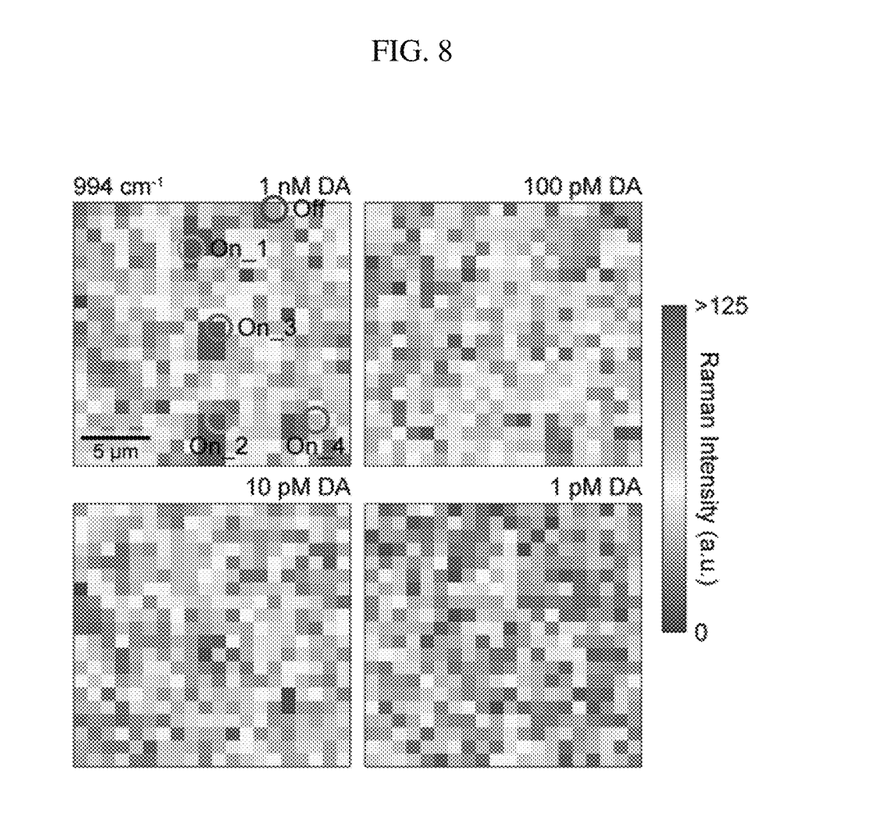
FIG. 8 is a diagram illustrating an image of an intensity of the 3-MPBA peak of DSP-NLPC+DA+3-MPBA-AuNP at various dopamine concentrations.

To evaluate the quantitative detection function of the double recognition structure by the surface-enhanced Raman spectroscopy complex probe, the NLPC substrates with dopamine-specific double recognition structures were mapped using dopamine at various concentrations from 1 pM to 1 nM. FIG. 8 is an image of the intensity of the 3-MPBA peak at 994 cm$^{-1}$, and each mapping image was obtained in a 20 μm×20 μm area of 20×20 pixels. As the dopamine concentration decreased, the number of pixels with high Raman intensity indicated by orange and red dots decreased gradually, but it can be seen that dopamine can be detected even at a pico-level concentration of 1 nM or less.

Figure 9:
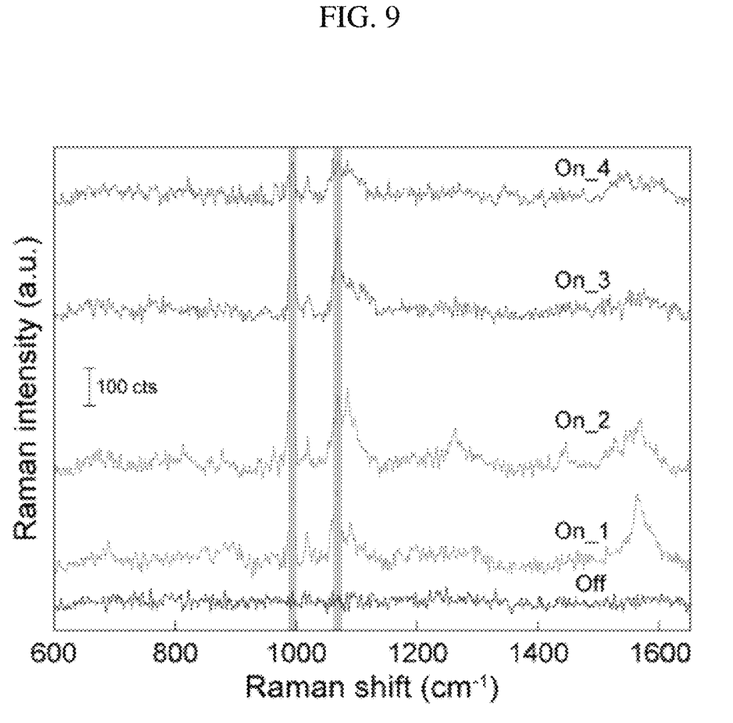
FIG. 9 is a diagram illustrating an "ON" spectrum in the presence of dopamine and an "OFF" spectrum in the absence of dopamine obtained from four positions illustrated in FIG. 8.

FIG. 9 is a diagram illustrating an "ON" spectrum in the presence of dopamine and an "OFF" spectrum in the absence of dopamine obtained from four positions illustrated in FIG. 8.

Figure 10:
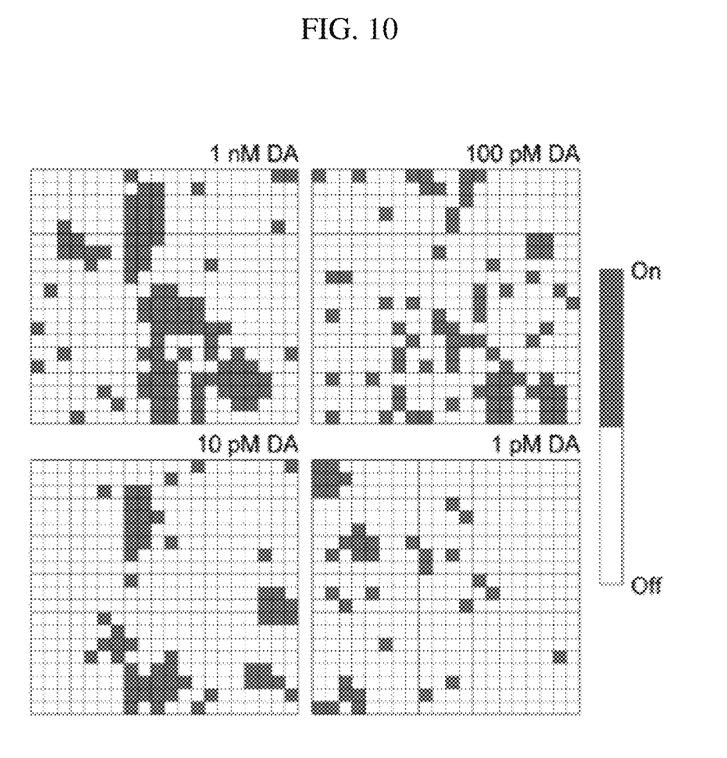
FIG. 10 is an image obtained as illustrated in FIG. 8, in which an SERS mapping result is converted into a binary signal by assigning "ON" or "OFF" to an intensity higher or lower than a predetermined threshold value.

Next, in the image obtained as illustrated in FIG. 8, the SERS mapping result is converted into a binary signal by assigning "ON" or "OFF" to an intensity higher or lower than a predetermined threshold value, and was illustrated in FIG. 10. Referring to FIG. 10, a digital version of the SERS mapping image using the 994 cm$^{-1}$ peak for various dopamine concentrations may be confirmed. Here, a gray "ON" pixel indicates the presence of dopamine, and a white "OFF" pixel indicates the absence of value. It is possible to perform the accurate quantitative measurement of the dopamine molecules possible through these digital images.

Figure 11:
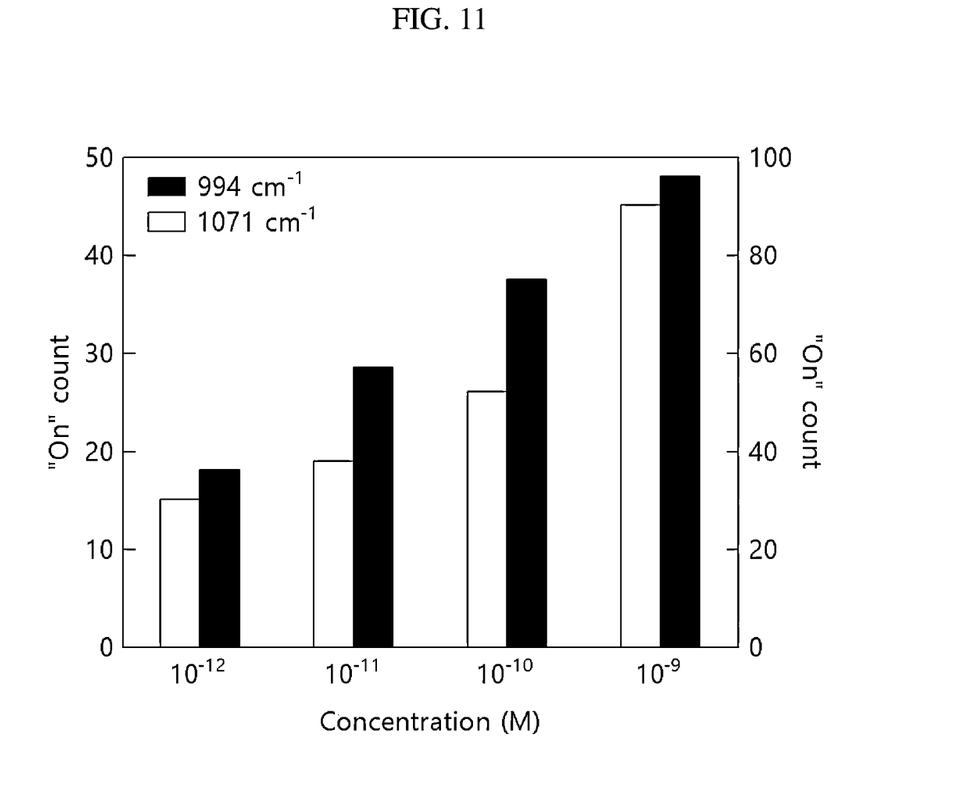
FIG. 11 is a graph showing the total number of "ON" pixels in each mapping image of FIG. 10 as a function.

FIG. 11 illustrates the total number of "ON" pixels in each mapping image of FIG. 10 as a function. As the dopamine concentration increased from 1 pM to 1 nM, the total number of "ON" pixels increased, and it was confirmed that the quantitative detection is possible even when the dopamine concentration was very low as $10^{-12}$.

Hereinabove, although the present invention has been described in detail through preferred examples and experimental examples, the scope of the present invention is not limited to specific examples, and should be construed according to the appended claims. In addition, those skilled in the art will understand that many modifications and variations are possible without departing from the scope of the present invention.

The invention claimed is:

1. A method of detecting catecholamine included in an analyte comprising:
    preparing a nano-laminate in which a plasmonic metal layer and an etching layer are alternately stacked, and a surface of the nanolaminate being modified with a compound that binds to a first functional group of catecholamine, and the nanolaminate comprises nanogap formed by etching the etching layer;

preparing a metal nanoparticle whose surface is modified with a compound that binds to a second functional group of the catecholamine;

incubating the nanolaminate, the metal nanoparticle, and catecholamine;

detecting a signal through Surface-enhanced Raman spectroscopy (SERS);

wherein the average diameter of the metal nanoparticles is smaller than the width of the nanogap, and the metal nanoparticles are attracted to the nanogap, thereby generating overlapping hot spots.

2. The method of claim 1, wherein the first functional group and the second functional group are each selected from an amine group or a diol group.

3. The method of claim 1, wherein the etching layer includes oxide or nitride.

4. The method of claim 1, wherein the etching layer is etched using a buffered oxide etchant (BOE) solution.

5. The method of claim 1, wherein the nanogap has a width of 1 nm to 20 nm.

6. The method of claim 1, wherein the metal nanoparticle is at least one selected from gold (Au), silver (Ag), copper (Cu), aluminum (Al), platinum (Pt), or palladium (Pd).

7. The method of claim 1, wherein the catecholamine binds to both the nanolaminate and the metal nanoparticle.

8. The method of claim 1, wherein the catecholamine includes at least one selected from dopamine, polydopamine, alpha-methyldopamine, norepinephrine, epinephrine, methyldopa, droxidopa, or 5-hydroxydopamine.

9. A method of providing information necessary for analyzing a concentration of catecholamine of an analyte for a diagnosis of neurological diseases comprising:

preparing a nano-laminate in which a plasmonic metal layer and an etching layer are alternately stacked, and a surface of the nanolaminate being modified with a compound that binds to a first functional group of catecholamine, and the nanolaminate comprises nanogap formed by etching the etching layer;

preparing a metal nanoparticle whose surface is modified with a compound that binds to a second functional group of the catecholamine;

incubating the nanolaminate, the metal nanoparticle, and catecholamine;

detecting a signal through Surface-enhanced Raman spectroscopy (SERS); and analyzing the concentration of catecholamine of the analyte;

wherein the average diameter of the metal nanoparticles is smaller than the width of the nanogap, and the metal nanoparticles are attracted to the nanogap, thereby generating overlapping hot spots.

10. The method of claim 9, wherein the neurological disease is Parkinson's disease, schizophrenia, attention deficit hyperactivity disorder, Huntington's disease, Lou Gehrig's disease, stroke, dementia, or epilepsy.

* * * * *